(12) United States Patent
Ugartemendia

(10) Patent No.: US 11,097,123 B1
(45) Date of Patent: Aug. 24, 2021

(54) ELECTRO-MAGNETIC STIMULATION DEVICE

(71) Applicant: Juan Jose Ugartemendia, Miami, FL (US)

(72) Inventor: Juan Jose Ugartemendia, Miami, FL (US)

(*) Notice: Subject to any disclaimer, the term of this patent is extended or adjusted under 35 U.S.C. 154(b) by 0 days.

(21) Appl. No.: 17/308,779

(22) Filed: May 5, 2021

(51) Int. Cl.
*A61N 2/06* (2006.01)
*A61N 2/08* (2006.01)
*A61N 2/00* (2006.01)

(52) U.S. Cl.
CPC ............. *A61N 2/008* (2013.01); *A61N 2/002* (2013.01)

(58) Field of Classification Search
CPC ........................................... A61N 2/06
See application file for complete search history.

(56) References Cited

U.S. PATENT DOCUMENTS 5,782,743 A * 7/1998 Russell ................... A61N 2/06
600/15

* cited by examiner

*Primary Examiner* — Christine H Matthews
*Assistant Examiner* — Joshua Daryl D Lannu
(74) *Attorney, Agent, or Firm* — Ruben Alcoba, Esq.

(57) ABSTRACT

An electro-magnetic stimulation device that alleviates the pain felt by a user when the device is placed on the user's body part that requires pain mitigation. The electro-magnetic stimulation device comprises of a leather chamois, a 99.99% led free copper plate that is attached to the leather chamois, a plurality of staggered magnetically connected magnets that are attached to the 99.99% led free copper plate, and an ionic solution that hydrates the leather chamois.

8 Claims, 3 Drawing Sheets

ELECTRO-MAGNETIC STIMULATION DEVICE

BACKGROUND

The present invention is an electro-magnetic stimulation device that is used to alleviate pain that does not require a battery or an electric power source to function.

On Earth, most life conceives, gives birth, grows, and evolves using the following two forces: 1. Magnetism, it protects us from the radiation produced from the sun and it also allows us to thrive on our planet; and 2. Electricity, the positive and negative electric charges that help line up and pre-arrange all matter, from the smallest molecules to the largest weather systems.

The inventor realized that since the above two forces were the driving forces of life, then why not make them work together for the better of humanity.

He figured that if he could combine the above two forces and apply them to the dermis of a human, then he could alleviate the pain we suffer due to either age or accidents that affect our limbs, arms, feet, back, and neck areas.

The present invention does not require an internal battery source or an external electrical source to power itself, for it uses the static electricity found in our atmosphere and the biological electricity we produce to power the device and produce an electro-magnetic field that loops within the areas of our body in which the device is placed.

The present invention is an electro-magnetic stimulation device that eliminates the need of having an internal battery source or an external battery source to function.

SUMMARY

The present invention is an electro-magnetic stimulation device that alleviates the pain felt by a user when the device is placed on the user's body part that requires pain mitigation.

The electro-magnetic stimulation device comprises of a leather chamois, a 99.99% la free copper plate that is attached to the leather chamois, a plurality of staggered magnetically connected magnets that are attached to the 99.99% la free copper plate, and an ionic solution that hydrates the leather chamois.

The present invention is used on a subject as follows: 1. Providing the device described above; 2. Hydrating the device with the ionic solution; 3. Placing the leather chamois on a section of the body of a user that requires pain mitigation; and 4. Keeping the device on the section of the body for a desired period that can be determined by the user.

An object of the present invention is to provide an electro-magnetic device that will alleviate pain.

Another object of the present invention is to provide an electro-magnetic device that will not require a battery or an external electrical power source.

DRAWINGS

These and other features, aspects, and advantages of the present invention will become better understood with regards to the following description, appended claims, and drawings where:

DESCRIPTION

Figure 1:
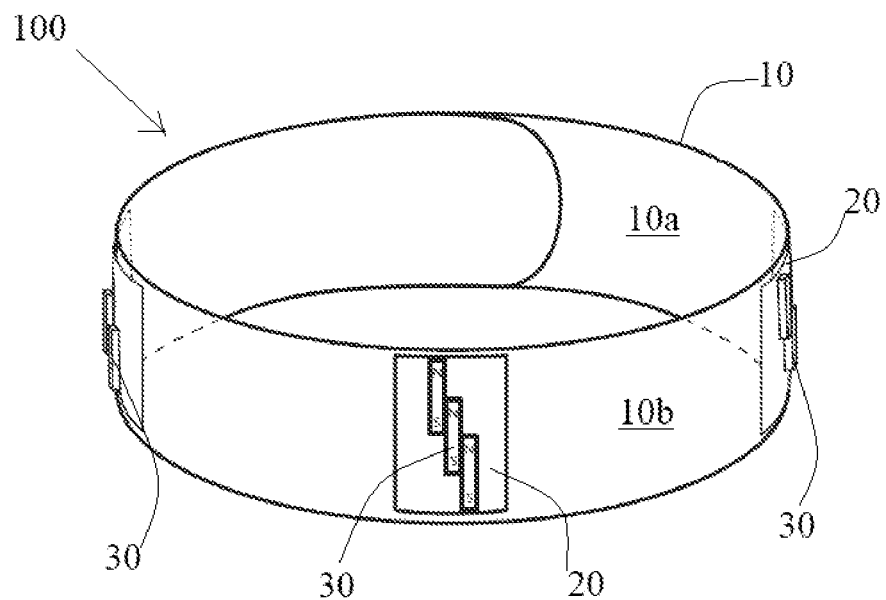
FIG. 1 shows a rear perspective view of the present invention.
Figure 2:
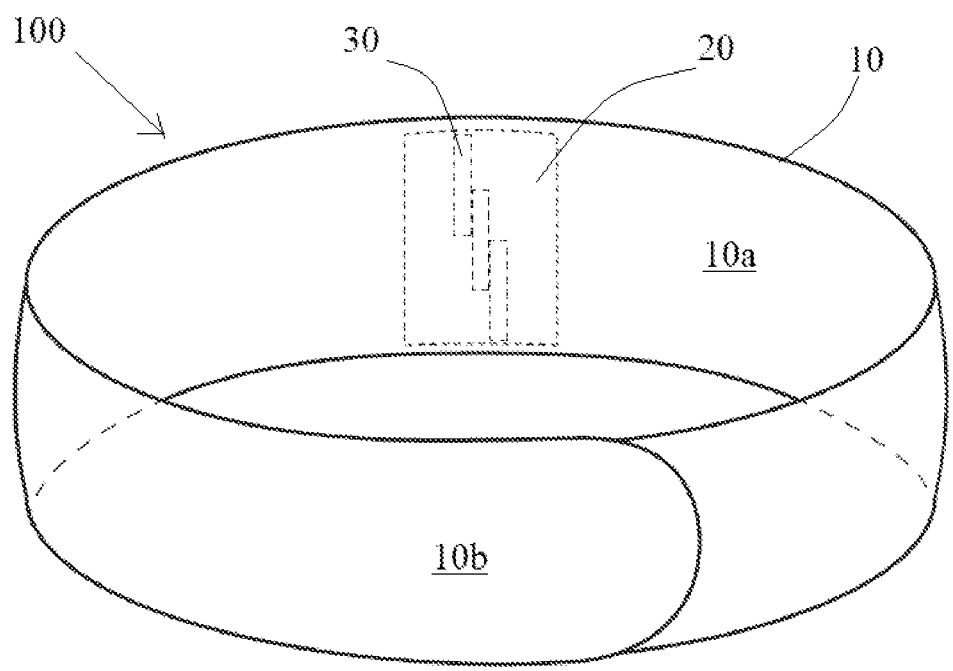
FIG. 2 shows a front perspective view of the present invention.
Figure 3:
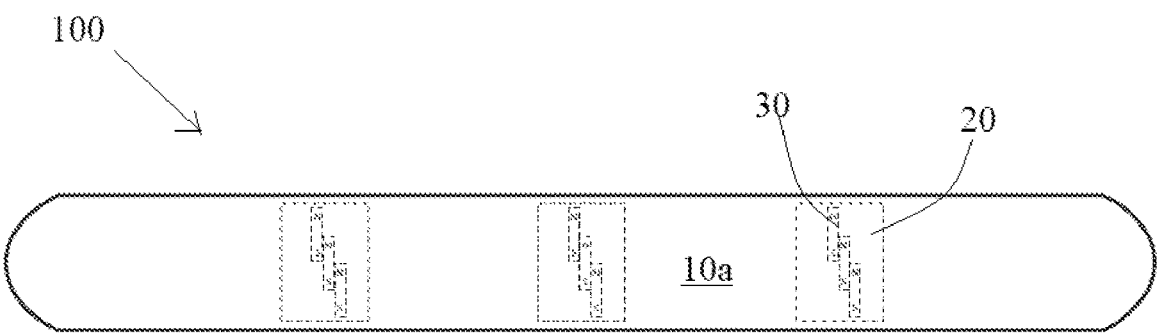
FIG. 3 shows a front side view of the present invention.
Figure 4:
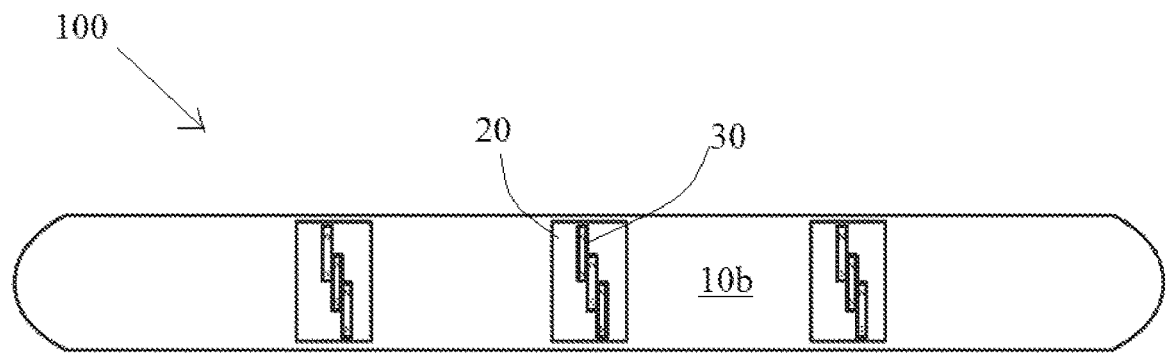
FIG. 4 shows a rear side view of the present invention.
Figure 5:
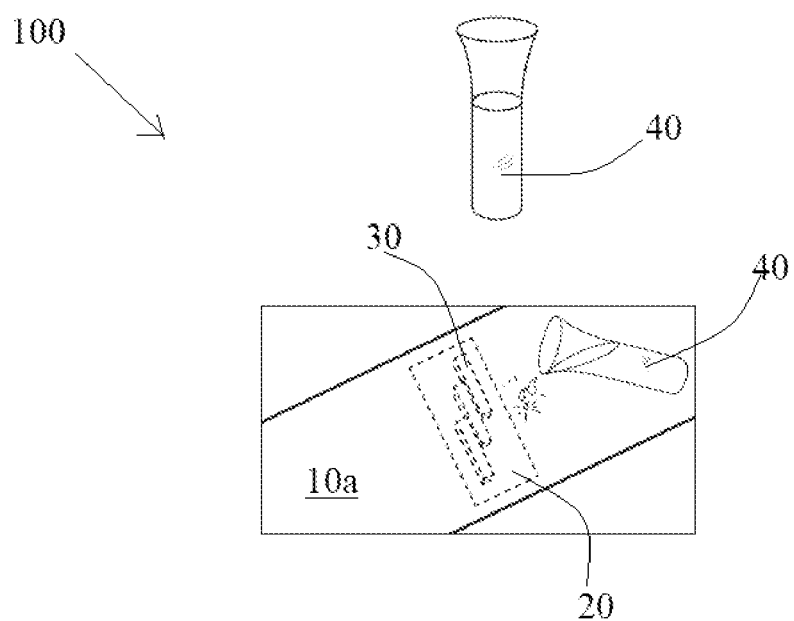
FIG. 5 shows a perspective view of all elements of the present invention.
Figure 6:
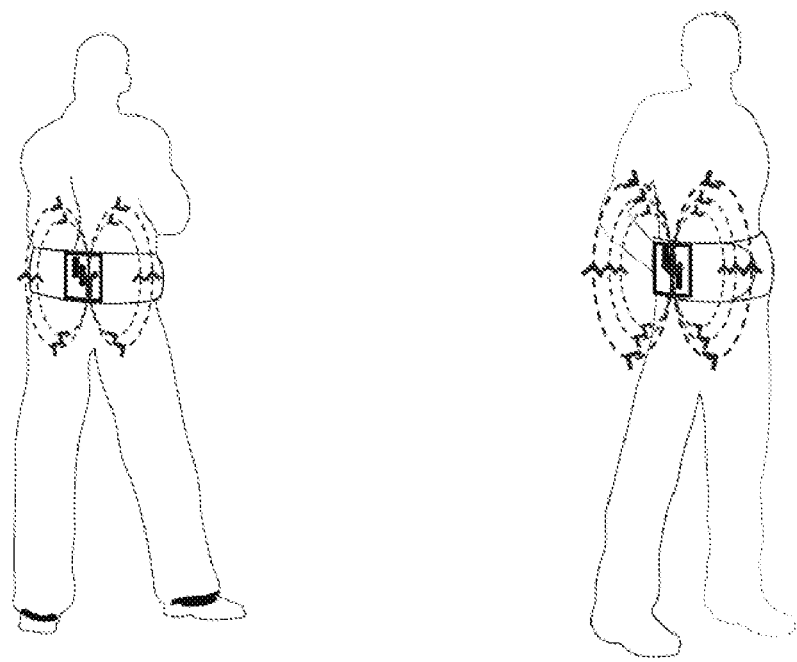
FIG. 6 shows perspective view of the device on a user.

As seen in FIGS. 1-6, the present invention is an electro-magnetic stimulation device 100 for alleviating pain.

The electro-magnetic stimulation device 100 comprises a leather chamois 10 that has a front side 10a and a rear side 10b. A 99.99% la free copper plate 20 that is attached to the rear side 10b of the leather chamois 10. A plurality of staggered magnetically connected magnets 30 that are attached to the 99.99% la free copper plate 20. And, an ionic solution 40 that hydrates the front side 10a leather chamois 10.

In an embodiment of the present invention, there will be a plurality of 99.99% lead free copper plates 20 that are linearly attached on the leather chamois 10 and each plurality of 99.99% lead free copper plates 20 has a plurality of staggered magnetically connected magnets 30 attached to each of the plurality of 99.99% la free copper plates 20.

In preferred embodiments, the ionic solution 40 is a magnesium sulfate solution.

In embodiments of the present invention, the leather chamois 10 is a belt.

Ina preferred embodiment, the magnets 30 are sixty mm in length by ten mm in width by three mm in thickness. In addition, the magnets 30 are made of a neodymium material that are N52 magnets.

In preferred embodiments, the invention is designed to produce up to five hundred millivolts.

In embodiments of the present invention, the copper plate 20 can be of other grades of copper.

The present invention is used by applying the leather chamois on the dermis of a user for a specific period that is determined based on the body part of the user. For example, if applying to the neck of a user, a period of five minutes may be sufficient. Yet, if applying to the back of a user, then it is recommended that the belt be placed on the user for a period of at least 30 minutes. The inventor, who at times sits for periods of 8 to 9 hours while sitting on a chair, uses the present invention for the duration of the 8 to 9 hours.

For the present invention to work optimally, the leather chamois 40 should be hydrated prior to use.

After the initial hydration of the leather chamois 10, the leather chamois 10 will be saturated with the magnesium sulfate, so in subsequent applications of the present invention, water may accomplish the hydration of the leather chamois 10, for the magnesium sulfate will be impregnated on the leather chamois 10. When the leather chamois 10 is saturated with the magnesium sulfate, the leather chamois 10 will be solid when dried, when in this state, then one only needs to apply water to the leather chamois 10 for it to generate the electro-magnetic field required to mitigate pain. When the leather chamois 10 no longer remains solid after repeated use, then the leather chamois 10 shall have to be recharged with the ionic solution 40.

The reason the inventor of the present invention chooses to use 99.99% lead free copper plate 20 rather than an impure copper plate is because he is conscious that if the copper was not of that purity, then he would be applying a lead poison to the user of the present invention.

In preferred embodiments of the present invention, the copper plate 20 of the present invention is either a 16 gauge, a 17 gauge, a 18 gauge, a 19 gauge, or a 20 gauge copper plate 20.

An advantage of the present invention is that it provides an electro-magnetic device that alleviates pain.

Another advantage of the present invention is that it provides an electro-magnetic device that does not require a battery or an external electrical power source.

While the inventor's above description contains many specificities, these should not be construed as limitations on the scope of the electro-magnetic stimulation device, but rather as an exemplification of several preferred embodiments thereof. Many other variations are possible. Accordingly, the scope should be determined not by the embodiments illustrated, but by the specification, the drawings, and the appended claims and their legal equivalents.

What is claimed is:

1. An electro-magnetic stimulation device for alleviating pain, the device comprising:
    a leather chamois that has a front side and a rear side;
    at least one 99.99% lead free copper plate that is attached to the rear side of the leather chamois;
    at least one plurality of staggered magnetically connected magnets that are attached to the at least one 99.99% lead free copper plate; and
    a magnesium sulfate solution that hydrates the front side of the leather chamois.

2. The electro-magnetic stimulation device for alleviating pain of claim 1, wherein
    the at least one 99.99% lead free copper plate is a a plurality of 99.99% lead free copper plates, and
    the at least one plurality of staggered magnetically connected magnets is part of a plurality of at least one plurality of staggered magnetically connected magnets, wherein the plurality of copper plates are linearly attached on the leather chamois, and each of the plurality of the at least one plurality of staggered magnetically connected magnets are attached to a copper plate of the plurality of 99.99% lead free copper plates.

3. The electro-magnetic stimulation device for alleviating pain of claim 2, wherein the leather chamois is a belt.

4. The electro-magnetic stimulation device for alleviating pain of claim 2, wherein the magnets are sixty mm in length by ten mm in width by three mm in thickness, and the magnets are made of a neodymium material.

5. An electro-magnetic stimulation device for alleviating pain, the device comprising:
    a leather chamois that has a front side and a rear side;
    at least one copper plate that is attached to the rear side of the leather chamois;
    at least one plurality of staggered magnetically connected magnets that are attached to the at least one copper plate; and
    a magnesium sulfate solution that hydrates the front side of the leather chamois.

6. The electro-magnetic stimulation device for alleviating pain of claim 5, wherein the at least one copper plate is a plurality of copper plates that are linearly attached on the leather chamois, and wherein the at least one plurality of staggered magnetically connected magnets is a plurality of at least one plurality of staggered magnetically connected magnets, wherein each of the plurality of the at least one plurality of staggered magnetically connected magnets are attached to a copper plate of the plurality of copper plates.

7. The electro-magnetic stimulation device for alleviating pain of claim 5, wherein the leather chamois is a belt.

8. The electro-magnetic stimulation device for alleviating pain of claim 5, wherein the magnets are 60 mm in length by 10 mm in width by three mm in thickness, and the magnets are made of a neodymium material.

\* \* \* \* \*